United States Patent [19]

Yanaihara et al.

[11] Patent Number: 5,712,105
[45] Date of Patent: Jan. 27, 1998

[54] MONOCLONAL ANTIBODY TO HUMAN GLICENTIN, HYBRIDOMA FOR PRODUCING SAID ANTIBODY AND ASSAY METHOD FOR HUMAN GLICENTIN USING SAID ANTIBODY

[75] Inventors: Noboru Yanaihara, Fujinomiya; Takeya Sato, Saitama-ken; Kiyoshi Fukuchi, Tokyo, all of Japan

[73] Assignee: Nisshin Flour Milling Co., Ltd., Tokyo, Japan

[21] Appl. No.: 548,152

[22] Filed: Oct. 25, 1995

[30] Foreign Application Priority Data

Oct. 31, 1994 [JP] Japan .................. 6-266567
Jul. 21, 1995 [JP] Japan .................. 7-185272

[51] Int. Cl.$^6$ .......... G01N 33/53; G01N 33/537; G01N 33/543; C07K 16/00
[52] U.S. Cl. .......... 435/7.94; 435/331; 435/346; 436/518; 530/387.9; 530/388.1; 530/388.24; 530/388.85; 530/389.2; 530/391.1; 530/391.3
[58] Field of Search .......... 435/240.27, 7.94, 435/331, 346; 436/518; 530/389.2, 391.1, 391.3, 387.9, 388.1, 388.24, 388.85

[56] References Cited

U.S. PATENT DOCUMENTS 4,376,110  3/1983  David et al. .................. 436/513
5,432,156  7/1995  Matsuno et al. .

FOREIGN PATENT DOCUMENTS 0 612 531  8/1994  European Pat. Off. .
0 635 573  1/1995  European Pat. Off. .
5-23196    2/1993  Japan .
6-80584    3/1994  Japan .

OTHER PUBLICATIONS

Aramaki, C., et al., Abstract JP05023196A (Feb. 2, 1993) (Abstract #1), 1993.
Aramaki, C., et al., Chemical Abstracts 118:189969 (Abstract #2) Abstract of JP05023196A, 1993.
Yanaihara, C., et al. Biomed. Res. (Japan), vol. 5/Suppl., pp. 19–32, 1984.
Kohler, G. and Milstein, C., Nature, vol.256, pp. 495–497, 1975.
Sevier, E. D., et al., Clin. Chem., vol. 27, No. 11, pp. 1797–1806, 1981.
Nakamura, R. M., et al. Enzyme immunoassays: Heterogeneous and homogeneous systems in: Handbook of Experimental Immunology (4th Edition) Blackwell Scientific Publications, pp. 27.1–27.20, 1986.
Seaver, S. Genetic Engineering News, vol. 14, pp. 10 and 21, Aug. 14, 1994.
Horm. Metab. Res., vol. 8, pp. 366–371, 1976, F. Sundby, et al., "Purification And Characterization of a Protein From Porcine Gut With Glucagon–Like Immunoreactivity".
Regulatory Peptides, vol. 2, p. 139, 1981, L. Thim, et al., "The Primary Structure Of Porcine Glicentin (Proglucagon)".
Nature, vol. 256, pp. 495–497, Aug. 7, 1975, G. Koehler, et al., "Continuous Cultures Of Fused Cells Secreting Antibody Of Predefined Specificity".

Primary Examiner—Christina Y. Chan
Assistant Examiner—Evelyn Rabin
Attorney, Agent, or Firm—Oblon, Spivak, McClelland, Maier & Neustadt, P.C.

[57] ABSTRACT

The present invention describes a monoclonal antibody which recognizes the C-terminal region of human glicentin. The antibody is useful for assaying for the presence of glicentin in a sample.

7 Claims, 3 Drawing Sheets

5,712,105

MONOCLONAL ANTIBODY TO HUMAN GLICENTIN, HYBRIDOMA FOR PRODUCING SAID ANTIBODY AND ASSAY METHOD FOR HUMAN GLICENTIN USING SAID ANTIBODY

FIELD OF THE INVENTION

This invention relates to a monoclonal antibody to human glicentin, a hybridoma cell capable of producing said monoclonal antibody and an assay method using an antibody to human glicentin (SEQ ID NO:1).

BACKGROUND OF THE INVENTION

On the basis of studies on glucagon, i.e. a polypeptide hormone comprising 29 amino acid residues, which is known to be secreted from the A cells of the islets of Langerhans in pancreas of animals and to activate adenylate cyclase system in cell membrane of liver and other organs, Sundby, F. et al isolated from porcine small intestine extract a polypeptide having a high molecular weight and an antigenicity to glucagon antibody and then named it "glicentin" [Sundby, F. et al., Horm. Metab. Res., Vol. 8, 366–371 (1976)]. Thereafter, Thim, L. and Moody, A. J. conducted its structural determination and elucidated that the glicentin comprises 69 amino acid residues and has the same amino acid sequence as glucagon in regard to the 33rd to 61st amino acid residues [Regulatory Peptides, Vol. 2, 139 (1981)]. Species difference could be seen in the amino acid sequences in glicentins. The amino acid sequence of human glicentin was later deduced from the DNA sequence of human preproglucagon.

Recently, the present inventors have made the production of human glicentin using genetic recombination technique (See, Japanese Patent Application No. 334126/1993, EP 0635573 A2) and it has been found upon further studies using the glicentin that it has a promoting action on insulin secretion (See, Japanese Patent Laid Open Application No. 80584/1994). Moreover, they have also found that human glicentin may increase the weight of mucous membrane and the length of villus of small intestine (Japanese Patent Application No. 326698/1993, EP 0612531 A1).

In order to elucidate and comprehend the relation between human glicentin and diabetes mellitus or gastrointestinal diseases or to perform diagnosis of such diseases, it would be medically very important to determine human glicentin with a good sensitivity specifically and distinguishably from other glucagon analogues. Thus, researchers attempted to selectively screen for glicentin by combining antibodies with different epitopes. As one of such attempts, there has been suggested a method described in Japanese Patent Laid Open Application No. 23196/1993 which was filed by the present applicant.

In the above Japanese Patent, there is disclosed an antibody capable of recognizing the C-terminal region of human glicentin using the immunogen obtained by forming a bound product of human glicentin obtained by genetic recombination technique and a carrier, e.g. Keyhole Limpet hemocyanin (hereinafter referred to as "KLH") according to a maleimide method, a glutaraldehyde method and others and admixing with Freund adjuvant. In this case, proteins such as albumin and the like may be also applied as a carrier. However, the resultant antibody could not always have a satisfactory binding reactivity to human glicentin.

Moreover, there was employed in the above Japanese Patent the immunogen obtained by synthesizing human glicentin C-terminal fragment (63–69) composed of 7 amino acid residues by means of a peptide synthesizer and combining the synthesized fragment with the carrier KLH according to the glutaraldehyde method. The fragment has the following amino acid sequence:

Arg Asn Arg Asn Asn Ile Ala (SEQ ID NO:2)

Although the monoclonal antibody GC-15 recognizing human glicentin C-terminal region as disclosed in the above Japanese Patent may determine human glicentin, its binding activity is not necessarily enough possibly due to the fact that the antigen having been applied for immunization is different from the natural one in its structure. Accordingly, there has been required an antibody having a higher binding reactivity to human glicentin.

Further, the above Japanese Patent discloses the monoclonal antibody GW17 obtained by using human glicentin having methionine incorporated at the N-terminal for immunization. However, this monoclonal antibody is classified as the antigen class of IgM and is unsuitable for specific determination of human glicentin according to the immunoassay using a sandwich method.

SUMMARY OF THE INVENTION

The present inventors have made earnest studies to solve the above-discussed problems and found out a method wherein human glicentin at a lower concentration can be specifically determined by producing the monoclonal antibody recognizing the C-terminal region of human glicentin and using it in combination with an antibody recognizing the N-terminal region. The present invention has been completed upon the above finding.

More specifically, the invention is directed to a monoclonal antibody to human glicentin having a recognition site in the positions from 51 to 69, especially from 51 to 62 in the amino acid sequence of human glicentin.

The invention is also directed to hybridoma 3D5A (FERM BP-5214) which is capable of producing said monoclonal antibody.

And further, the invention is directed to a determination or assay method of human glicentin wherein an anti-human glicentin antibody is immobilized, the immobilized antibody is reacted with a human glicentin-containing sample to form a complex of the immobilized antibody with human glicentin and then the complex is reacted with a labelled anti-human glicentin antibody which is different from the immobilized antibody in the recognition site to bind the labelled antibody to said complex, and an amount of the bounded labelled antibody is determined, characterized in that either said immobilized antibody or said labelled antibody is derived from said monoclonal antibody. In the above-mentioned human glicentin assay method, the labelled antibody to be used may include a human glicentin antibody labelled with an enzyme or a radioisotope.

DETAILED DESCRIPTION OF THE INVENTION

Figure 1:
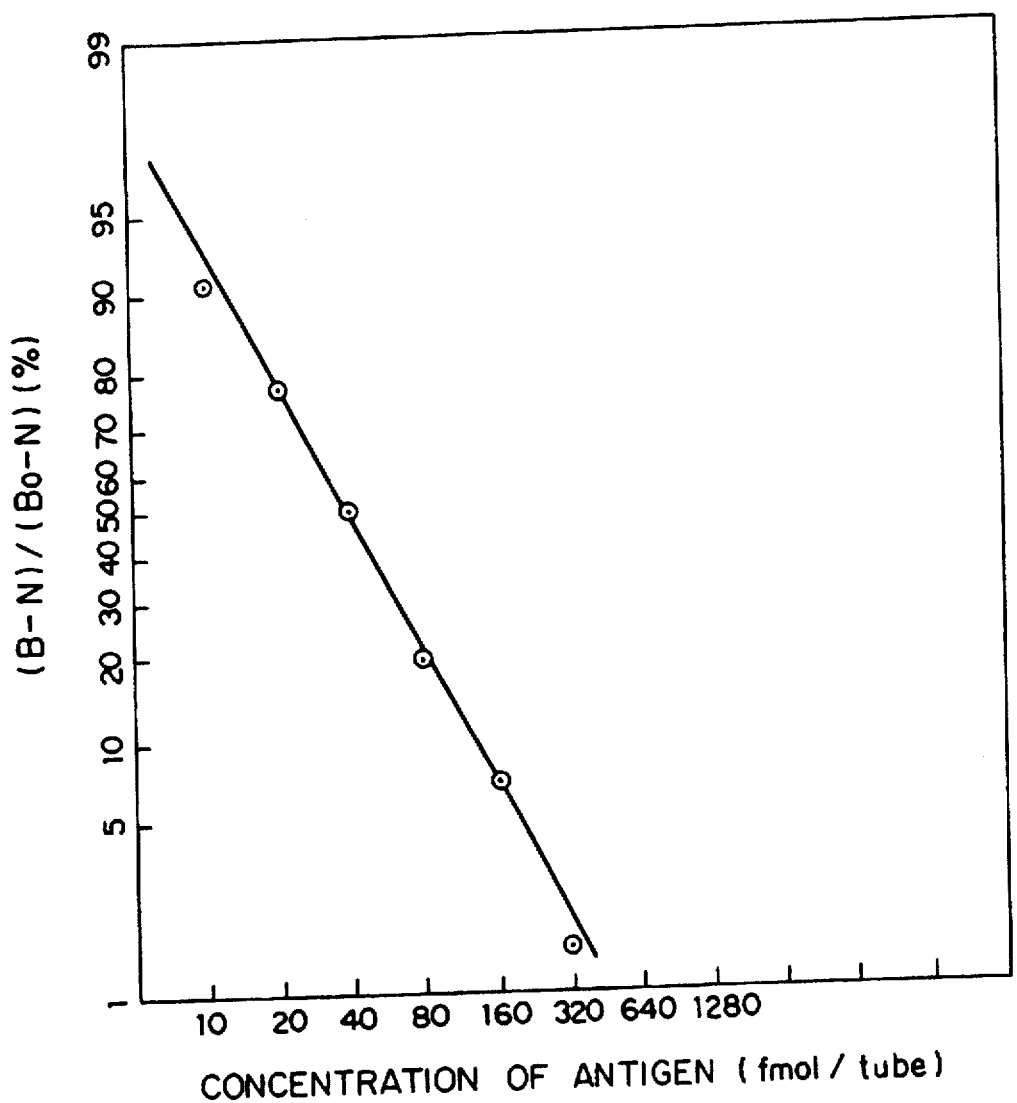
FIG. 1 is a standard curve showing the relation between concentrations of genetic recombinant human glicentin as a standard antigen and (B—N)/(B$_0$—N) values.

The amino acid sequence region of human glicentin according to the invention may be divided into the N-terminal region of the 1st to 32nd amino acids from the N-terminal of human glicentin and the C-terminal region of the 33rd to 69th amino acids from the N-terminal of human glicentin.

The present inventors have obtained the monoclonal antibody recognizing the C-terminal of human glicentin in the course of a specific immunoassy of human glicentin. Heretofore, antiserum recognizing the C-terminal could only be accidentally obtained and the monoclonal antibody recognizing said region had a weak reactivity up to the present time. However, an antibody having a strong reactivity has become constantly available by obtaining hybridoma cell 3D5A which may produce a monoclonal antibody having a far stronger reactivity to said region.

The present monoclonal antibody can be produced by using the cell obtained from selection of hybridomas produced according to the so called cell fusion method. More specifically, a fused hybridoma is formed between antibody-producing cells and myeloma cells, said hybridoma is cloned and a clone capable of producing a specific antibody to human glicentin is selected to produce the present antibody. Antibody-producing cells in accordance with this invention include, for example, spleen cells, lumphonodus cells, B lymphocyte cells and other cells isolated from animals immunized with human glicentin.

The antigen used for immunization of animals may be human glicentin purified from human digestive tract and human glicentin produced by genetic engineering technique or chemical synthesis may be also used.

In order that an antigen may be presented in the state close to the natural type human glicentin, the present inventors have utilized a whole amino acid sequence structure adsorbed onto an adsorbent such as cellulose, polyvinylidene fluoride, a vinyl polymer, agarose, an ion exchange resin and others, when a whole structure of the amino acid sequence of human glicentin is utilized as an antigen.

Thus, they have succeeded in the production of an antibody having a strong binding property to human glicentin by employing the human glicentin adsorbed onto polyvinyl pyrrolidone and obtained according to genetic engineering procedure as an immunogen for immunization of antibody-producing cells.

The antibody-producing cells, i.e. the animal spleen cells and myeloma cells immunized with the above-mentioned antigen can be cell-fused according to general procedures such as polyethylene glycol, Sendai virus, electric pulse and others [See, Nature, Vol. 256, 495–497 (1975) et al.]. The resulting hybridoma can be screened according to an enzymatic antibody method and others and cloned according to a limiting dilution method.

In the invention, the hybridoma 3D5A capable of producing a monoclonal antibody to human glicentin can be formed as described above.

The resulting hybridoma 3D5A was applied for deposit in the National Institute of Bioscience and Human-Technology Agency of Industrial Science and Technology, Ministry of International Trade and Industry, 1–3, higashi 1-chome, Tsukuba-shi, Ibaraki-ken 305 Japan, and accepted with Accession Number FERM P-14575 on Oct. 6, 1994 and transferred to international deposit with Accession Number FERM BP-5214 on Aug. 31, 1995.

The so obtained clone is incubated in a suitable medium for growth. Alternatively, it may be intraperitoneally transplanted to mice given pristane beforehand and the ascites bearing a monoclonal antibody at a high concentration is recovered. The monoclonal antibody is purified from the cultured broth or murine ascites thus obtained according to salting-out with ammonium sulfate, ion exchange chromatography, gel chromatography, affinity chromatography using protein A and others.

The anti-human glicentin monoclonal antibody thus obtained is extremely suitable for a specific assay for human glicentin or other glucagon analogues bearing a recognition region as an antigen in a living body.

On the basis of the anti-human glicentin monoclonal antibody obtained as above, the specific determination method of human glicentin according to this invention has been completed in sandwich method in combination of said antibody with a polyclonal antibody or monoclonal antibody having a recognition site for the region of the human glicentin amino acid sequence different from that of said monoclonal antibody. In this case, specific determination may be also accomplished by a combination of said monoclonal antibody with an antiserum.

Namely, the present human glicentin assay can be accomplished by specific determination of human glicentin according to the assay method using sandwich method such as enzyme-linked immunosorbent assay (ELISA method) using two or more combined antibodies, immunoradiometric assay (IRMA method) and others.

In the present method, an antibody is immobilized with microplates or beads to a solid phase and allowed to react with a test solution containing human glicentin and the human glicentin bound to a solid phase is assayed according to an enzyme immunoassay using a different antibody. For instance, aliquot of human glicentin or an unknown amount of an aqueous sample (e.g. serum, plasma, tissue extract and others) is allowed to react with the present anti-human glicentin monoclonal antibody of a solid phase formed on microplates and assay is performed by luminescent reaction such as color reaction, fluorescent reaction, bioluminescent reaction or chemical reaction or radioactivity using a labelled second antibody. As the solid phase human glicentin antibody, there may be employed those antibodies derived from other monoclonal antibody than the present anti-human glicentin monoclonal antibody or polyclonal antibody, and, as the labelled second antibody, those derived from the present human glicentin monoclonal antibody.

Solid phase of the antibody is formed using any well-known chemical binding method or physical adsorption method. Chemical binding method may include, for example, a glutaraldehyde method or a method using two crosslinking agents such as a maleimide method using N-succinimidyl-4-(N-maleimidomethyl)cyclohexane-1-carboxylate, N-succinimidyl-2-maleimidoacetate and the like, a carbodiimide method using 1-ethyl-3-(3-dimethylaminopropyl)-carbodiimide hydrochloride and the like.

Alternatively, a complex may be formed beforehand by reacting a test substance with two sorts of antibodies having different epitopes and then captured by forming a solid phase of a third antibody to said antibodies according to the above-mentioned method.

Labelling of antibody may be performed according to a method for direct binding of enzyme such as β galactosidase, horse radish peroxidase and the like to antibody. Alternatively, an antibody may be labelled with biotin and then an avidin- or streptoavidin-bound enzyme may be applicable. Alternatively, an anti-murine IgG labelled antibody may be used for enzyme-labelled antibody such as monoclonal antibody. And, there may be used an antibody labelled with a radioisotope such as $^{125}I$, $^{131}I$, $^3H$ and the like.

This invention will be illustrated by way of the following examples. However, these examples are given for illustration purposes only and it should not be construed that they are limiting the scope of this invention.

EXAMPLE 1

Production of monoclonal antibody and study on specificity of said antibody

1) Preparation of immunogen

Recombinant human glicentin produced using *E. coli* was used. This recombinant human glicentin has the following amino acid sequence given in SEQ ID NO:1 in the sequence listing.

The present inventors used the human glicentin adsorbed on polyvinyl pyrrolidone in order that the antigen could be expressed in the state similar to natural human glicentin.

More specifically, 3.9 mg of human glicentin was dissolved in 100 µl of physiological saline and 3 ml of 50% polyvinyl pyrrolidone (Merck A. G., Darmstadt, Germany). The mixture was stirred at room temperature for 2 hours to have human glicentin adsorbed on polyvinyl pyrrolidone. Then, 3 ml of Freund's complete adjuvant (Carbiochem Behring Diagnostics, La Jolla, Calif., U.S.A.) was added and the resulting mixture was stirred on an ice bath for 15 minutes by means of an omnimixer (Sotvail, Du Pont, France) to prepare an immunization injection for 4 mice.

2) Immunization

BALB/c female mice of 6 weeks old were ether-anesthetized, disinfected with alcohol systemically and injected subcutaneously at some dozen or so points in the body surface with 0.5 ml of the immunization injection (120 µg in terms of human glicentin).

After 3 weeks from the priming, 1st booster was performed by subcutaneous injection of 0.25 ml of the immunization injection (60 µg in terms of human glicentin). After further 3 weeks, 2nd booster was performed. After 1 week from the 2nd booster, blood sample was collected from the tail end of mice and the antibody titer in serum was determined according to radioimmunoassay (RIA). Following the same procedure as described above in the subsequent immunization schedule, boosters were performed four times. RIA was carried out according to the following procedure: As a standard diluent was used 0.01M phosphate buffer (pH 7.4) containing 0.14M sodium chloride, 0.025M ethylenediaminetetraacetic acid (hereinafter referred to as "EDTA"), 0.5% bovine serum albumin (hereinafter referred to as "BSA") and 0.02% sodium azide. After 0.5 ml of the standard diluent was added to 50 µl of the supernatant of the cultured broth, 0.1 ml of $^{125}$I-human glicentin (5,000 cpm in terms of radioactivity) was admixed and the reaction was carried out at 4° C. overnight. Thereafter, 0.1 ml of normal mouse serum (diluted to 200 times) and 0.1 ml of goat anti-mouse IgG serum (diluted to 10 times), both of which were prepared with the standard diluent respectively, and 0.5 ml of 5% polyethylene glycol 6000 dissolved in 0.01M phosphate buffer (pH 7.4) containing 0.14M sodium chloride and 0.02% sodium azide were added and then the reaction was carried out at 4° C. for 2 hours. After centrifugation (3,000 rpm, 30 minutes, 4° C.), the supernatant was suction-filtered, and radioactivity of the sediment was measured by means of a γ ray counter (Aroka Co., Ltd., Japan, ARC-1000).

For final immunization, human glicentin was dissolved in sterile physiological saline to a concentration of 0.2 µg/µl, and 100 µl of this solution (20 µg in terms of human glicentin) was administered to mice at the tail vein.

3) Preparation of medium 450 ml of RPMI 1640 medium was used as a complete medium after adding 55 mg of a sodium pyruvate solution, 5 ml of a streptomycin-penicillin solution (penicillin 10,000 units/ml, streptomycin 10,000 µg/ml), 5 ml of 0.2M L-glutamine, 0.25 ml of 0.25M 2-mercaptoethanol and 50 ml of fetal bovine serum having inactivated complements by treating at 56° C. for 30 minutes. Also, 98 ml of the complete medium containing 2 ml of a hypoxanthine-aminopterin-thymizine (hereinafter referred to as "HAT") solution of a 50-fold concentration was used as HAT medium. Further, 98 ml of the complete medium containing 2 ml of a hypoxanthine-thymidine (hereinafter referred to as "HT") solution of a 50-fold concentration was used as HT medium.

The PEG solution was used which was prepared by adding 1.5 ml of the serum free RPMI 1640 medium to 1.5 g of polyethylene glycol 4000, dissolving them on a water bath at 80° C., allowing to cool in an incubator at 60° C. and sterilizing it by filtering in a clean bench by means of a filter of 0.22 µm.

4) Preparation of spleen cells

After 3 days from the final immunization, spleen was aseptically excised from mouse under non-anesthesia. The excised spleen was transferred to 5 ml of a complete medium and, after connective tissues were removed, it was transferred to a fresh complete medium. After spleen was incised by means of scissors, spleen cells were extruded by means of a stainless wire net of 60 mesh. The cell suspension was obtained by filtration to remove cellular mass and others. The suspension was transferred into a plastic tube and centrifuged (1,000 rpm, 3 minutes). Then, the supernatant was suction-filtered and 20 ml of serum free RPMI 1640 medium was added. The mixture was centrifuged and serum free RPMI 1640 medium was added so as to be the number of cells of $1\times10^8$ cells/ml.

5) Preparation of myeloma cells

Myeloma P3U1 cells derived from mouse was suspended in serum free RPMI 1640 medium and collected by centrifugation (1,000 rpm, 3 minutes). Then, they were prepared with serum free RPMI 1640 medium so as to be the number of cells of $1\times10^7$ cells/ml.

6) Cell fusion

Myeloma cells and spleen cells were taken in 1 ml portions in a 50 ml plastic tube to be a ratio of 1:10 in cell number and then centrifuged (1,000 rpm, 3 minutes). The supernatant was completely removed by suction filtration, the sediment was slightly loosened and 1 ml of the PEG solution warmed to 37° C. was slowly added over about 2 minutes. Then, 2 ml of the complete medium was slowly added over about 5 minutes. 15 ml of the HAT medium was added, the supernatant was removed by centrifugation (1,000 rpm, 5 minutes), the sediment was washed with 20 ml of the HAT medium and diluted so as to be $1\times10^6$ cells/ml in terms of spleen cell. The diluted mixture was poured into a 24-well plate in 1.5 ml portion per well and incubated in a CO$_2$ incubator at 5% CO$_2$ and 37° C.

7) Screening

The cells implanted into the plate were exchanged in a half amount with the HAT medium on the 7th day after the starting of incubation and in a half amount with the HT medium on the 15th day. On the 17th day, it was similarly exchanged in a half amount with the HT medium. On the 20th day, it was exchanged in a half amount with the complete medium and then incubation was continued with the complete medium.

The supernatant was collected from each well and it was confirmed according to the above-mentioned RIA whether or not an antibody might be produced.

The cells in the plate which were confirmed to produce an antibody were repeatedly selected according to the limiting dilution method as explained below.

The cells were suspended by pipetting and then diluted with the complete medium to be the number of cells of $1\times10^3$ cells/ml and further diluted with the complete medium to be the numbers of cells of 10 cells/ml and 50 cells/ml. It was added to a 96-well plate to which rat thymocytes had been added at 0.1 ml/well and incubated in a $CO_2$ incubator. The antibody in the supernatant was confirmed according to the above-mentioned RIA and then clonings were repeated until the antibody titers of the supernatants in every well reached almost uniform to obtain the hybridoma 3D5A capable of producing a monoclonal antibody.

8) Determination of subclass

The subisotype of the monoclonal antibody produced by the hybridoma 3D5A was determined for the hybridoma incubation supernatant after cloning according to the ELISA using an anti-mouse IgG subclass set (available from Zymet Co., Ltd., U.S.A., MONOAb-ID™ EIA KIT). The results are shown in the following Table 1.

TABLE 1

| Class | Subclass | Type |
|---|---|---|
| IgG | IgG 1 | K |

9) Preparation of the present monoclonal antibody

The hybridoma 3D5A thus prepared was incubated, $1\times10^7$ cells were suspended in 1 ml of physiological saline and the suspension was administered intraperitoneally to female BALB/c mice given intraperitoneally 0.5 ml of pristane before 7–30 days. Ascites was collected at the time when the abdomen of mouse was sufficiently expanded and the activity of mouse was depressed. The ascites thus collected was transferred into a sterilized plastic tube and centrifuged (1,000 rpm, 3 minutes) to recover the cells. The supernatant was transferred to another tube and centrifuged (3,000 rpm, 10 minutes) to remove fatty components floating over the surface.

The ascites bearing the antibody was admixed with 1 ml of a combining buffer (1.5M glycine, 3M sodium chloride, pH 8.9) and the mixture was adsorbed onto a Protein A Econopack® cartridge made by Bio-Rad Co., Ltd., U.S.A.. Unadsorbed fractions were again adsorbed onto the cartridge and washed with 30 ml of the combining buffer. The cartridge was eluted with 20 ml of an eluting buffer (0.1M citrate, pH 6), on which the eluate was immediately neutralized with 1 ml of 1M Tris buffer (pH 8.0).

The resulting anti-human glicentin monoclonal antibody was regarded as the monoclonal antibody 3D5A.

10) Preparation of standard curve

A standard curve was prepared according to the measurements using the RIA.

The genetic recombinant human glicentin having the amino acid sequence given in SEQ ID NO:1 in the sequence listing was used as a standard antigen. $^{125}$I-human glicentin was as a labelled antigen and the monoclonal antibody 3D5A was at a final dilution ratio of 56,000 times. As a standard diluent was used 0.01M phosphate buffer (pH 7.4) containing 0.14M sodium chloride, 0.025M EDTA, 0.5% BSA and 0.02% sodium azide. Separation of the liberated $^{125}$I-human glicentin (separation of B/F) was performed in the presence of polyethylene glycol according to double antibody technique. Determination of samples was performed twice on each sample and an average value was calculated.

More specifically, 0.4 ml of a standard diluent, 0.1 ml of the standard antigen diluted with the standard diluent or the sample solution, 0.1 ml of a diluted anti-glicentin antibody solution, 0.1 ml (5,000 cpm) of labelled antigen $^{125}$I-human glicentin were admixed in a glass tube and the reaction was carried out at 4° C. overnight. Then, 0.1 ml of normal mouse serum (diluted to 200 times), 0.1 ml of goat anti-mouse IgG serum (diluted to 10 times), which were prepared with a standard diluent respectively, and 0.5 ml of 5% (w/v) polyethylene glycol 6000 dissolved in 0.01M phosphate buffer containing 0.14M sodium chloride and 0.02% sodium azide were admixed in turn and the reaction was carried out at 4° C. for 2 hours. After centrifugation (3,000 rpm, 30 minutes, 4° C.), the supernatant was suction-filtered off, and the radioactivity of the sediment was determined by a γ ray counter (Aroka Co., Ltd., Japan, ARC-1000) and regarded as a combined count (B). Separately, a mixture of 0.5 ml of a standard diluent, 0.1 ml of a diluted antibody solution and 0.1 ml of a diluted labelled antigen solutuion, and a mixture of 0.6 ml of a standard diluent and 0.1 ml of a diluted labelled antigen was prepared, the reaction was carried out by a similar technique. B/F separation was performed and the respective radioactivities were regarded as the maximum combined count ($B_0$) and the non-specific combined count (N). A standard curve had the $(B—N)/(B_0—N)$ values on the Y axis and standard antigen concentrations on the X axis. The standard curve linear-regressed on a logit-log scale showed a good linearity. The results are shown in FIG. 1.

11) Study on specificity

Specificity of the monoclonal antibody obtained according to the invention was studied using glicentin related peptides. The glicentin related peptides used include human glucagon, human glucagon (1–18), human glucagon-like peptides [GLP-1(7–36)—$NH_2$], human glicentin (63–69), and they were diluted with a standard diluent and measured according to the above-mentioned RIA. A dose-response curve was prepared from the results and the value obtained by dividing the standard peptide concentration exerting a 50% inhibitory activity by the peptide concentration exerting a 50% inhibitory activity was defined as cross reactivity of the peptide. The results are shown in the following Table 2.

TABLE 2

| Peptides | Cross reactivity (%) |
|---|---|
| Human glicentin | 100* |
| Human glucagon [= glicentin (33–61)] | 25.7 |
| Human GLP-1 (7–36)-$NH_2$ | 0 |
| Human glucagon (1–18) [= glicentin (33–50)] | 0 |
| Human glicentin (63–69) | 0 |

*Cross reactivity to glicentin defined as 100%

It is apparent from the above results that the monoclonal antibody 3D5A has the recognition site in the positions from 51 to 62 in the amino sequence of human glicentin and does hardly or not react with GLP-1.

EXAMPLE 2

Determination by ELISA

1) Preparation of monoclonal antibody solid phase plate

IgG fraction of the monoclonal antibody GC-15 or 3D5A recognizing the C-terminal region of human glicentin was diluted to a concentration of 10 µg/ml per protein with 50 mM phosphate buffer (pH 7.0). The solution was poured in 50 µl portions into each well in a 96-well plate (available from Nunc Co., Ltd., Denmark) and it was allowed to stand at 4° C. overnight to fix the antibody onto the plate. The wells were washed three times with PBS (0.01M phosphate buffer, pH 7, 0.15M sodium chloride) and then 25%(v/v) digested casein solution diluted four times with distilled water was added in 300 µl portions to each well, which was then allowed to stand at 37° C. for 2 hours to perform blocking.

2) Biotinylation of antibody

The monoclonal antibody GN4-1 IgG fraction recognizing the N-terminal region of human glicentin was equilibrated to a 50 mM sodium borate solution in water (pH 8.6) to prepare a concentartion of 1 mg/ml per protein. Using 1.5 ml of the antibody solution, biotinylation was carried out by means of a biotinylation kit available from Amersham Co., Ltd. according to the instructions from the manufacturer. After completion of the reaction, the reaction mixture was passed through a prepacked-Sephadex® G25 column (available from Pharmacia AB) equilibrated with PBS containing 0.1% BSA to separate the antibody from unreacted biotinylation reagent. The biotinylated antibody thus prepared was stored at 4° C. after thimerosal was added to the solution so as to be a final concentration of 0.01%.

3) Determination

Figure 2:
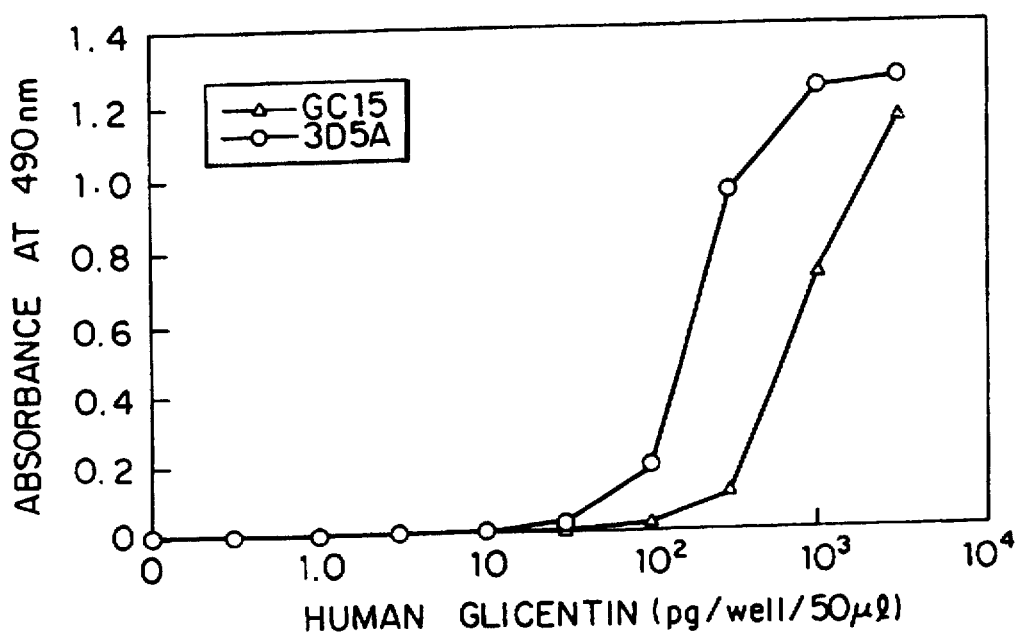
FIG. 2 is a graph showing the relation between concentrations of human glicentin in the sample and amounts of absorbance.

The plate prepared according to the above-mentioned method was repeatedly washed three times with PBS, a purified human glicentin preparation was stepwise-diluted from 60 ng/ml to 0.02 ng/ml with PBS containing 0.1% BSA and 50 µl of the solution was placed onto each well. The reaction was carried out at room temperature for 2 hours. The reaction mixture was again washed well with PBS, 50 µl of the biotinylated antibody diluted to 1,200 times with PBS containing BSA was placed onto each well and the reaction was carried out at room temperature for 2 hours. Then, the plate was washed well with PBS containing 0.05% Tween 20, 50 µl of a streptavidin.peroxidase (available from Vector Co., Ltd., U.S.A.) solution diluted to 4,000 times with PBS containing 0.1% Tween 20 and the mixture was allowed to stand at room temperature for one hour. Then, o-phenylenediamine was dissolved in 0.1M citrate potassium hydroxide buffer (pH 4.5) to a concentration of 1 mg/ml and hydrogen peroxide was added so as to be a final concentration of 0.012% to form a color reagent. The plate was washed well with PBS containing 0.05% Tween 20 and then 100 µl of the color reagent was added to develop color at room temperature. The reaction was stopped by the addition of an equivalent amount of 2N sulfuric acid and absorbance was measured at a wave length of 490 nm. The results are shown in FIG. 2.

EXAMPLE 3

Determination by IRMA

1) Preparation of monoclonal antibody solid phase plate

The monoclonal antibody 3D5A IgG fraction recongnizing the C-terminal of human glicentin as obtained according to the procedure described in Example 1 was diluted to a concentration of 10 µg/ml per protein with 50 mM phosphate buffer (pH 7.0). This solution was poured in 200 µl portion/each well onto a 96-well plate (available from Nunc Co., Ltd., Denmark) and it was allowed to stand at 4° C. overnight to fix the antibody onto the plate. The wells were washed three times with purified water, 300 µl of 25%(v/v) digested casein solution diluted to four times with distilled water was added to each well and it was allowed to stand at 37° C. for 2 hours to perform blocking.

2) Iodination of antibody

Polyclonal antibody antiserum NR2 recognizing the N-terminal region of human glicentin was purified using Sepharose 4B column having combined human glicentin and the resulting IgG fraction was equilibrated to a 50 mM sodium phosphate solution in water so as to be a concentration of 80 µg/0.1 ml. To the antibody solution were added in turn 4 µl (14.4 MBq) of Na [$^{125}$I] and 5 µl of Chloramine-T (1 mg/ml) and the reaction was carried out at room temperature for 10 minutes. The reaction was stopped by the addition of 5 µl of ascorbic acid (10 mg/ml) and 5 µl of 10% potassium iodide. Purification was performed by passing the reaction mixture through Sephadex® G-25 (available from Pharmacia AB) column (0.8×25 cm) equilibrated with 0.1M Tris hydrochloric acid buffer (pH 8.5) to separate the antibody from unreacted Na [$^{125}$I]. The labelled antibody thus prepared was stored at 4° C.

3) Determination

Figure 3:
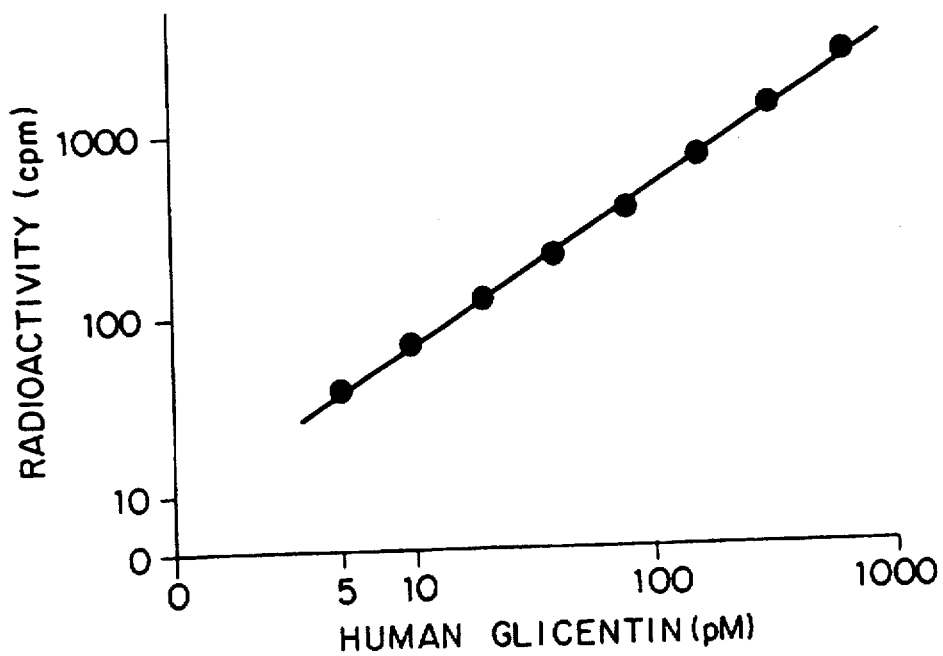
FIG. 3 and 4 are graphs showing the relation between concentrations of human glicentin in the samples and amounts of radioactivity.

The plate prepared according to the above-mentioned method was washed three times with purified water and the purified human glicentin preparation stepwise diluted from 5 pM to 640 pM with 50 mM citrate buffer (pH 5.0) containing 10% horse serum, 0.14M sodium chloride and 0.02% sodium azide or the test sample was poured into wells in 200 µl portions for every well. The reaction was carried out at 4° C. for more than 8 hours., Then, the plate was again washed well with purified water and the labelled antibody diluted to 100,000 cpm/0.2 ml with 50 mM citrate buffer (pH 5.0) containing 10% horse serum and 0.02% sodium azide was placed into wells in a 200 µl portion per well. The reaction was carried out at 4° C. for more than 16 hours. Then, the plate was washed well with purified water, dried and the radioactivity bound to solid phase was measured by means of a well-type γ counter. The results are shown in FIG. 3. A standard curve showed a good linearity in the range of 5–640 pM on a log-log scale with the minumum detection sensitivity of 5 pM.

Human glicentin concentrations in the plasma of normal man were determined from estimation on the results obtained according to the prior determination method and considered to be 30–50 pM. Thus, the present determination system is the system with a good sensitivity which can detect human glicentin concentration in the plasma of normal man.

4) Reproduction test

In order to investigate stability of the above determination system, coefficient of variation during determination and that between determinations were investigated. The results are shown in the following Table 3.

TABLE 3

| Human glicentin (pM) | n | Coefficient of variation during determination (%) | Coefficient of variation between determinations (%) |
|---|---|---|---|
| 10 | 3 | 3.5 | 4.8 |
| 40 | 3 | 4.5 | 4.7 |
| 160 | 3 | 3.2 | 3.0 |

Both coefficients of variation during determination and between determinations are within the range of not more than 5%, which demonstrates the present determination system is stable.

5) Study on specificity

Determination was performed according to the above-mentioned determination system using human oxyntomodulin, human glucagon or human GLP-1(7–36)-amide instead of the authentic sample, human glicentin. The results are shown in the following Table 4.

TABLE 4

| Peptide | Cross reactivity |
|---|---|
| Human glicentin | 100% |
| Human oxyntomodulin | 0 |
| Human glucagon | 0 |
| Human GLP-1(7–36)-NH2 | 0 |

As can be seen from the Table 4, it has been demonstrated that no glicentin related peptides could be detected and thus the present determination system is specific to human glicentin.

6) Addition and recovery test using human plasma

Human glicentin was added to human plasma so as to be at 5, 10, 40 and 160 pM's, respectively, and determination was performed according to the above-mentioned method. The results are shown in the following Table 5.

TABLE 5

| Amount of glicentin added (pM) | Recovery (%) |
|---|---|
| 5 | 94.2 |
| 10 | 112.8 |
| 40 | 108.9 |
| 160 | 113.4 |

It has been shown that the results of the addition and recovery tests are good within the range of concentrations as investigated.

7) Dilution test

Figure 4:
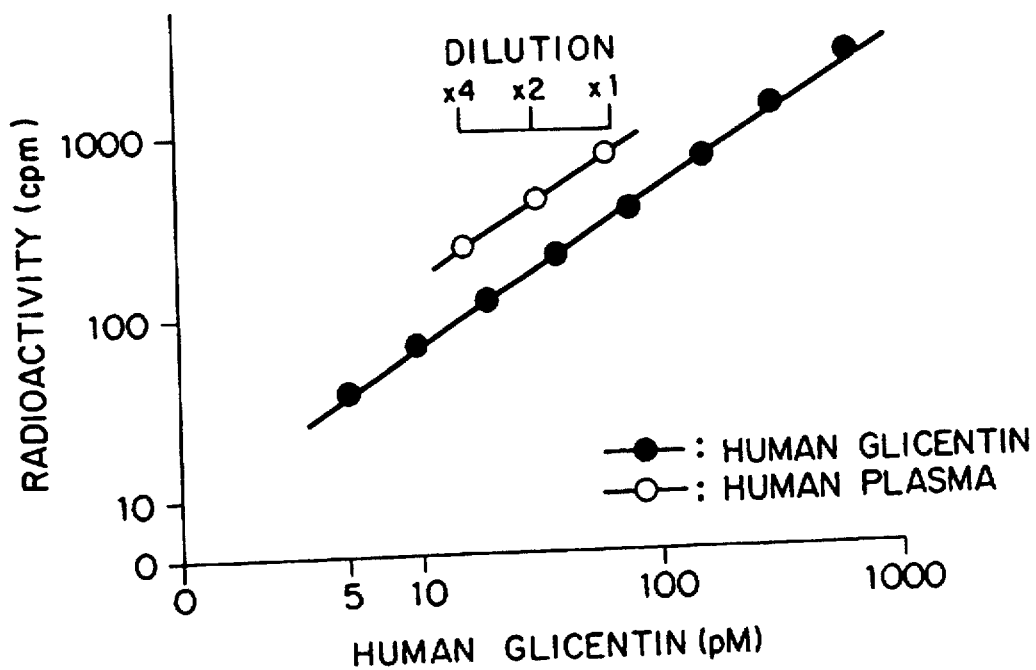

To human plasma was added human glicentin at 160 pM and the mixture was stepwise diluted to twice and four times with 50 mM citrate buffer (pH 5.0) containing 10% horse serum, 0.14M sodium chloride and 0.02% sodium azide. The diluted mixture was determined according to the method as described in the above item 3). The results are shown in FIG. 4. The dilution curve of the human glicentin-containing plasma is found to be parallel to the standard curve and it has been demonstrated that human glicentin in plasma could be determined by the present determination system.

From the results of the addition and recovery test and dilution test, it has been proven that the present determination method for human glicentin can specifically and directly determine human glicentin in human plasma.

What is claimed is:

1. A hybridoma having Accession No. BP-5214.

2. A monoclonal antibody produced by the hybridoma having Accession No. BP-5214.

3. A method for detecting human glicentin in a sample comprising the steps of;
   (a) providing a sample containing human glicentin;
   (b) providing a first antibody and a second antibody, wherein the first antibody or the second antibody is a monoclonal antibody produced by the hybridoma having Accession No. BP-5214;
   (c) attaching the first antibody to a support, thereby immobilizing the first antibody;
   (d) contacting the sample with the first antibody, thereby forming a first immunological complex including human glicentin and the first antibody;
   (e) contacting the first immunological complex with the second antibody, thereby forming a second immunological complex including human glicentin, the first antibody, and the second antibody; and
   (f) detecting human glicentin in the second immunological complex.

4. The method of claim 3, wherein the second antibody contains a label.

5. The method of claim 4, wherein the label contains a radioisotope.

6. The method of claim 4, wherein the label contains biotin.

7. The method of claim 6, wherein the detecting step comprises contacting the second antibody with labeled avidin or labeled streptavidin.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 69 amino acids
    ( B ) TYPE: amino acid
    ( D ) TOPOLOGY: linear ( i i ) MOLECULE TYPE: protein ( x i ) SEQUENCE DESCRIPTION: SEQ ID NO:1:

```
Arg Ser Leu Gln Asp Thr Glu Glu Lys Ser Arg Ser Phe Ser Ala Ser
 1               5                  10                  15

Gln Ala Asp Pro Leu Ser Asp Pro Asp Gln Met Asn Glu Asp Lys Arg
                20                  25                  30

His Ser Gln Gly Thr Phe Thr Ser Asp Tyr Ser Lys Tyr Leu Asp Ser
            35                  40                  45

Arg Arg Ala Gln Asp Phe Val Gln Trp Leu Met Asn Thr Lys Arg Asn
        50                  55                  60

Arg Asn Asn Ile Ala
65
```

( 2 ) INFORMATION FOR SEQ ID NO:2:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:2:

-continued

```
Arg Asn Arg Asn Asn Ile Ala
 1               5
```